(12) United States Patent  
Wilson

(10) Patent No.: US 9,491,972 B2  
(45) Date of Patent: Nov. 15, 2016

(54) SEXUAL NOVELTY DEVICE WITH A SMOKING PIPE

(71) Applicant: CPI NOVELTIES, INC., Tyler, TX (US)

(72) Inventor: Wayne Wilson, Flint, TX (US)

(73) Assignee: CPI NOVELTIES, INC., Tyler, TX (US)

( * ) Notice: Subject to any disclaimer, the term of this patent is extended or adjusted under 35 U.S.C. 154(b) by 775 days.

(21) Appl. No.: 13/767,264

(22) Filed: Feb. 14, 2013

(65) Prior Publication Data

US 2014/0224263 A1   Aug. 14, 2014

(51) Int. Cl.
*A61F 5/41* (2006.01)
*A24F 3/00* (2006.01)

(52) U.S. Cl.
CPC . *A24F 3/00* (2013.01); *A61F 5/41* (2013.01); *A61F 2005/411* (2013.01); *A61F 2005/414* (2013.01)

(58) Field of Classification Search
CPC .............. A24F 1/00; A24F 7/00; A24F 1/08; A24F 13/00; A24F 13/02; A24F 3/00; A61H 19/44; A61H 2201/165; A61F 5/41

See application file for complete search history.

(56) References Cited

U.S. PATENT DOCUMENTS

| | | | | |
|---|---|---|---|---|
| 4,200,114 A | * | 4/1980 | Waite | A24F 13/14 131/178 |
| 4,243,058 A | * | 1/1981 | Gershbein | A24F 3/00 131/176 |
| 2004/0025884 A1 | * | 2/2004 | McKown | A61M 16/0666 128/207.18 |
| 2013/0111952 A1 | * | 5/2013 | Ra | A44C 9/02 63/6 |

* cited by examiner

*Primary Examiner* — Christine H Matthews
(74) *Attorney, Agent, or Firm* — Greer, Burns & Crain, Ltd.

(57) ABSTRACT

A sexual novelty device includes a mouthpiece and a penile band. The mouthpiece has a generally tubular housing that defines an inner chamber dimensioned for receiving a smoking pipe. An insertion opening in the housing is configured for accommodating insertion of the smoking pipe. An inhalation opening at a first end of the housing is in fluid communication with the chamber and is configured for providing access to the smoking pipe by a user. The penile band is associated with the housing, and constructed and arranged for resiliently engaging a penis.

14 Claims, 4 Drawing Sheets

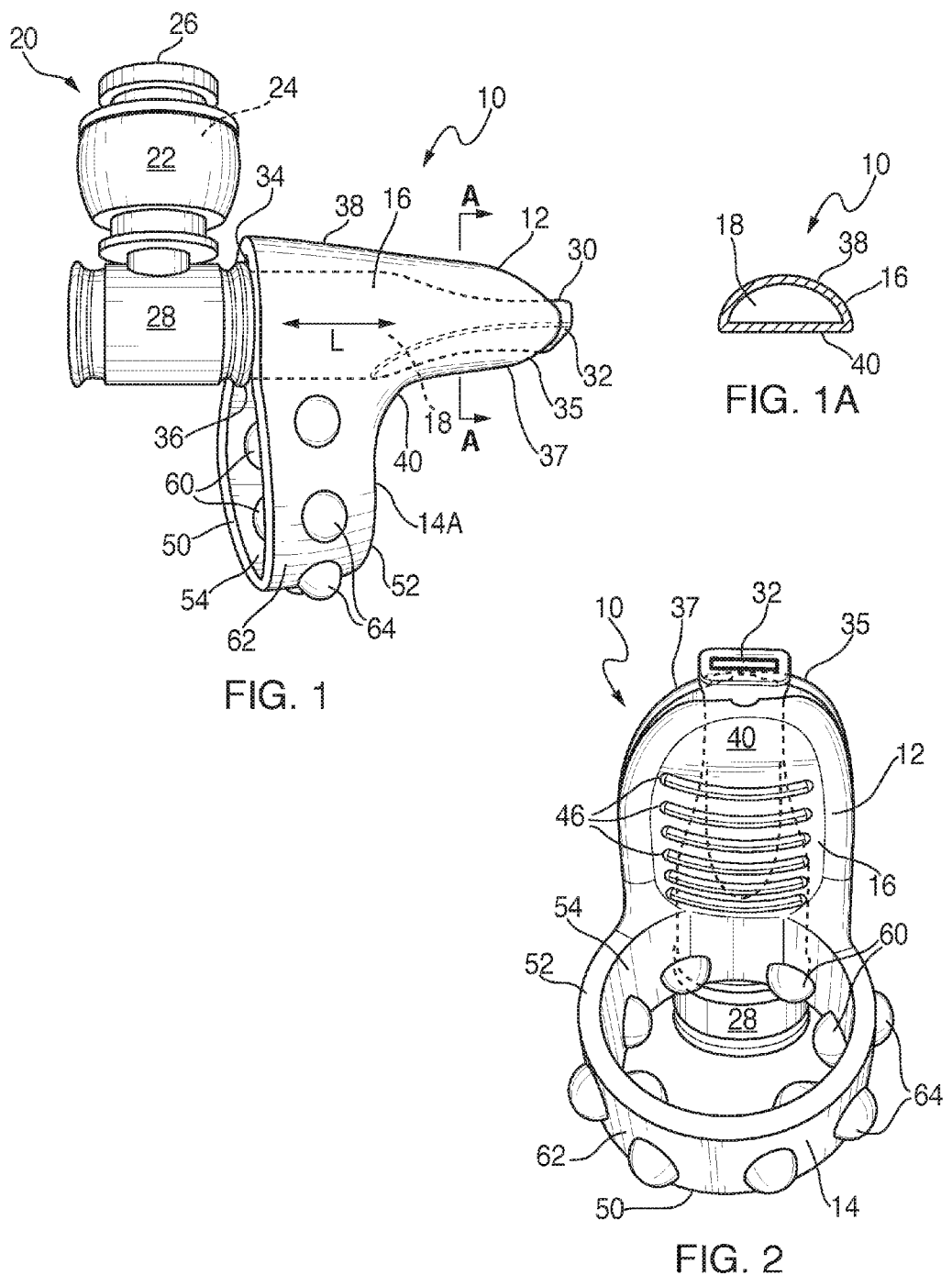

SEXUAL NOVELTY DEVICE WITH A SMOKING PIPE

BACKGROUND

The present device relates to erection aids, and particularly to an erection aid for prolonging an erection of a penis while simultaneously facilitating smoking activities, and also for dealing with premature ejaculation in men.

A commercial penile ring is typically wrapped around an erect penis to primarily slow down a flow of blood from the penis, thereby maintaining an erection for a longer duration. Also known as a cock ring, it can be selectively worn around either the penis or a scrotum. The ring can be made of many different materials, such as leather, rubber, or silicone.

SUMMARY

The present sexual novelty device features a mouthpiece for holding a smoking pipe, and a penile band for providing a prolonged erection. It is preferred that the mouthpiece and the penile band are formed unitarily, such as by molding. In use, the penile band is elastically expanded and placed around a shaft portion of a penis, exposing a head and an inner foreskin layer. In a similar fashion to conventional penile rings, the band traps blood inside the penis to maintain an erection. However, at the same time, the present mouthpiece receives the smoking pipe so that a partner can smoke and simultaneously perform sexual activities such as fellatio. Due to the sustained compression around a dorsal area of the penis, a wearer can maintain the erection while the partner enjoys the use of the pipe. The partner, or multiple partners can utilize the pipe in turn, thereby promoting enhancement of an erectile function as the partner(s) orally stimulate the exposed areas of the penis while smoking.

More specifically, the present sexual novelty device includes a mouthpiece and a penile band. Included in the mouthpiece is a generally tubular housing that defines an inner chamber dimensioned for receiving a smoking pipe. An insertion opening in the housing is configured for accommodating insertion of the smoking pipe, and an inhalation opening at a first end of the housing in fluid communication with the chamber is configured for providing access to the smoking pipe by a user. The penile band is associated with the housing, and is constructed and arranged for resiliently engaging a penis.

In another embodiment, a sexual novelty device is provided that includes a smoking pipe and a holder. The holder includes a mouthpiece and a penile band. A generally tubular housing in the mouthpiece defines an inner chamber dimensioned for receiving the smoking pipe. An insertion opening in the housing is configured for accommodating insertion of the smoking pipe, and an inhalation opening at a first end of the housing in fluid communication with the chamber is configured for providing access to the smoking pipe by a user. The penile band is associated with the housing, and is constructed and arranged for resiliently engaging a penis.

BRIEF DESCRIPTION OF THE DRAWINGS

FIG. 1 is a side perspective view of an exemplary first embodiment of a sexual novelty device in accordance with the present disclosure;

FIG. 1A is a fragmentary cross-sectional view taken along the line A-A of FIG. 1 and in the direction generally indicated;

FIG. 2 is a bottom perspective view of the sexual novelty device of FIG. 1;

DETAILED DESCRIPTION

Figure 3:
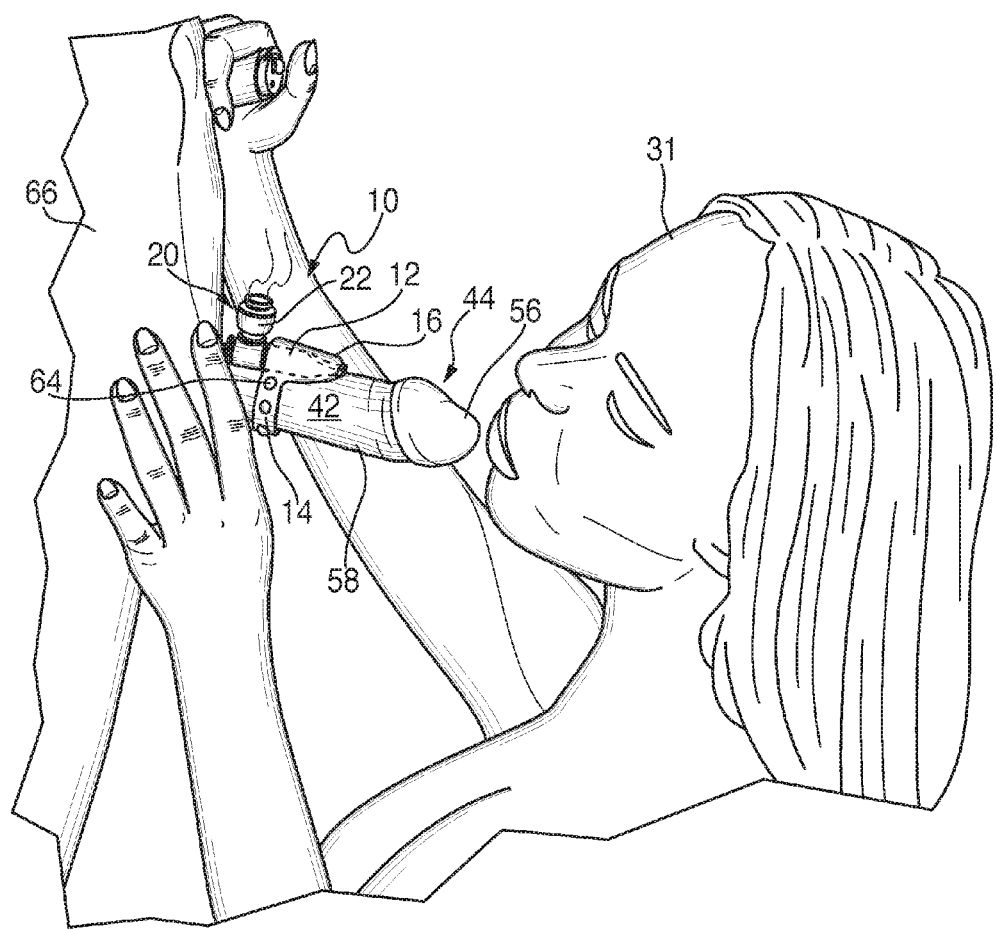
FIG. 3 is a first illustration of the sexual novelty device of FIG. 1 in use.

Referring now to FIGS. 1-2, a sexual novelty device is generally designated 10 and has a mouthpiece or a holder 12 and a penile band 14. A generally tubular shaped housing 16 in the mouthpiece 12 defines an inner chamber 18 dimensioned for receiving a smoking pipe, generally designated 20. The sexual novelty device 10 is preferably made of any elastic material including at least one of silicone, natural rubber, synthetic rubber, copolymerized rubber, and elastomer. Further, it is preferred that that the present device 10 is molded, as by injection molding or the like, such that the mouthpiece 12 and the penile band 14 are integrally formed. However, it is also contemplated that the penile band 14 is attachable to the mouthpiece 12 by chemical adhesives, ultrasonic welding or other conventional fastening techniques. While a standard metal smoking pipe 20 is shown for illustrative purposes only, it is contemplated that the present device 10 is useful with any kind of smoking pipe that fits into the inner chamber 18.

As an example, the pipe 20 includes segmented members, which can be assembled using complementary helically threaded portions for connecting segments to each other. A first member is a pipe bowl 22 which defines a cavity 24 for receiving a combustible material, and also has an apertured cap 26 through which the combustible material is ignited. The bowl 22 is threadably connected directly onto a second member, a pipe shank 28. Then, a third member, a stem 30 is threadably fastened onto the shank 28. A lip 32 of the stem 30 is in fluid communication with the bowl 22 and the shank 28, such that smoke can be drawn from the bowl 22 to the lip 32 for user inhalation.

During use, an exterior of the pipe 20 typically becomes heated due to a frequent ignition of the combustible material, such as tobacco. To protect the user from the generated heat, the housing 16 thermally insulates at least one of the shank 28 and the stem 30. Depending on a size of the housing 16 that encloses the segmented members, only the stem 30 or both the shank 28 and the stem 30 are encapsulated in the chamber 18. In any case, the housing 16 encloses at least the stem 30 portion of the pipe 20.

Referring now to FIGS. 1-4, a flexible nature of the housing 16 allows the housing 16 to elastically and detachably grip at least one of the shank 28 and stem 30 portions of the pipe 20 for rotatably securing the pipe 20 in the chamber 18. As depicted in FIG. 1, the bowl 22 is oriented generally vertically, or at a 12 o'clock position relative to the housing 16. Thus, a right-handed person can position the bowl 22 slightly to the right when viewed from the perspective of a partner 31 as seen in FIG. 3, approximately 1-2 o'clock compared to a standard vertically positioned bowl, for easier access to the holed cap 26 for ignition. Similarly, a left-handed partner 31 can position the bowl 22 slightly to the left, approximately 10-11 o'clock, when igniting the combustible material.

In one embodiment, the pipe 20 is slidably inserted into an insertion opening 34 of the housing 16 such that the lip 32 of the pipe 20 reaches an inhalation opening 35. Although the insertion opening 34 is optionally placed anywhere in the housing 16, it is preferred that the insertion opening is usually located at a distal end 36 of the housing 16 and is dimensioned for accommodating insertion of the pipe 20 into the chamber 18.

A proximate end 37 of the housing 16 has the inhalation opening 35 in fluid communication with the chamber 18 and configured for providing access to the smoking pipe 20 by a user. A diameter of the inhalation opening 35 is smaller than the corresponding dimension of the insertion opening 34. Formed as a flexibly closable slit, the inhalation opening 35 is configured for facilitating user inhalation of smoke from the stem 30 of the pipe 20. Thus, the user can readily perform smoke inhalation from the pipe 20 by drawing air from the inhalation opening 35. Additionally, because the slit 35 is flexible and elastic, it is retractable along a longitudinal axis of the mouthpiece 12 towards the insertion opening 34, partially exposing the stem 30 for direct access to the pipe 20 for the user. It will be seen, from FIG. 1, that in the device 10, the housing 16 preferably tapers towards the inhalation opening 35.

Figure 4:
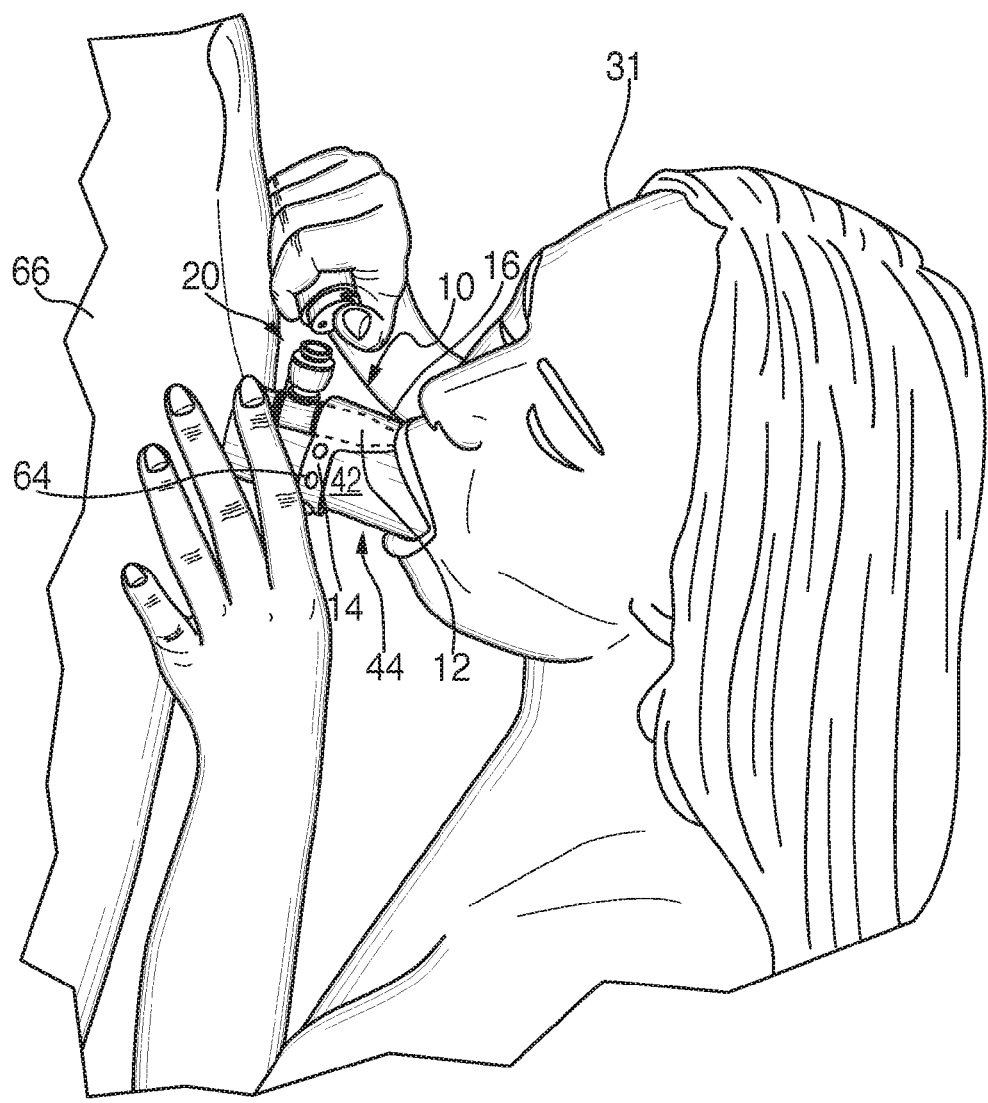
FIG. 4 is a second illustration of the sexual novelty device of FIG. 1 in use.

Although the housing 16 is contemplated as being any geometric shape, such as cylindrical, cuboid, triangular, or cone or pyramid, an exemplary vertical cross-section, generally "D"-shaped housing 16 is shown in FIG. 1A. A first surface 38 of the housing 16 is substantially dome-shaped in vertical cross-section, and a second surface 40 of the housing 16 is substantially flat. A shaft 42 of a penis, generally designated 44 (as shown in FIGS. 3-4), directly abuts the second surface 40.

In the preferred embodiment, the second surface 40 includes a friction formation 46, preferably a plurality of spaced, parallel ribs that extend transversely to a longitudinal axis of the mouthpiece 12 for improving friction between the second surface 40 and the shaft 42. This enhanced friction prevents slippage of the mouthpiece 12 from the penis 44 during use, even when the penis is lubricated. Any type of textured ribs, ridges, grooves, or bumps are contemplated for disposition as the friction formation 46 on the second surface 40 for enhancing friction in this manner. Further, the angular orientation and/or spacing of the ribs 46 is variable to suit the situation.

Referring again to FIGS. 1-4, the penile band 14 is associated with the housing 16 and also is constructed and arranged for resiliently engaging the penis 44. It is contemplated that, while preferably molded in silicone, the present penile band 14 is optionally fabricated of any kind of stretchable strip, belt, ring, fabric wrap, rubber, leather and the like made from a flat, web-like material. A width of the band 14 is variable depending on how long the band extends along a longitudinal direction "L" of the mouthpiece 12. For example, the penile band 14 has a length extending at least approximately ⅓ a length of the mouthpiece 12 when the housing 16 encloses only the stem 30 portion of the pipe 20. Positioning of the band 14 can also vary with respect to the housing 16. Generally speaking, the band 14 is fixedly attached to the second surface 40 of the housing 16, and is substantially closer to the insertion opening 34 than the inhalation opening 35. A diameter of the band 14 is preferably larger than the diameter of the housing 16, depending on the size of the pipe 20.

Referring again to FIGS. 1-4, the band 14 has an entry end 50 and an exit end 52. Both ends 50, 52 are configured for slidingly accommodating the penis 44. In the preferred embodiment, the entry end 50 is generally aligned with the insertion opening 34 located at the distal end 36 of the housing 16. However, it is contemplated that both ends 50, 52 can be disposed anywhere relative to the second surface 40 of the housing 16 as long as space is available for attachment of the band 14.

An interior surface 54 of the band 14 engages and elastically wraps around the shaft 42 portion of the penis 44, exposing glans 56 and foreskin layer 58 of the penis 44 for sexual stimulation. A beaded region 60 is preferably formed on the interior surface 54 for increasing friction between the band 14 and the shaft portion 42 and thus helping to maintain penile erection by restricting a blood flow from dorsal vein and artery of the penis 44. The interior surface 54 is dimensioned for fitting around the shaft 42 portion of the penis 44 but also behind testicles for repressing premature ejaculation and prolonging erection of the penis 44.

An exterior surface 62 of the band 14 is preferably provided with at least one gripping formation 64 for enhancing the ability of the user or the partner 31 to grasp the band when engaged on the penis shaft portion 42. Such gripping formations are especially helpful when the penis is lubricated. While the preferred device 10 is provided with hemispherical beads as the gripping formation 64, other shapes, sizes and spacing of the formations is contemplated as long as gripping is enhanced. For example, the optional formations 64 include at least one of ribs, bumps, straight-, wavy-, and zigzag-lined areas. The formations 64 as well as the beaded region are optionally spaced regularly or irregularly on the corresponding exterior and interior surfaces 62, 54 of the penile band 14. Further, the second surface 40 of the housing 16 is optionally provided with the hemispherical gripping formations 64 in lieu of the friction formation 46.

Referring now to FIGS. 3-4, an exemplary use of the present sexual novelty device 10 is illustrated. A wearer 66 puts on the device 10 by gently stretching the band 14 to fit any sized penis 44. Because the device 10 is made of soft material, such as silicone, it provides great comfort. His partner 31 ignites the combustible material in the bowl 22 and draws smoke from the bowl 22 to the lip 32 for inhalation. At the same time, the partner 31 performs fellatio on the wearer 66 by sexually stimulating the wearer's penis 44 using her tongue and lips. Thus, the partner simultaneously enjoys the smoking and the sexual activities.

Figure 5:
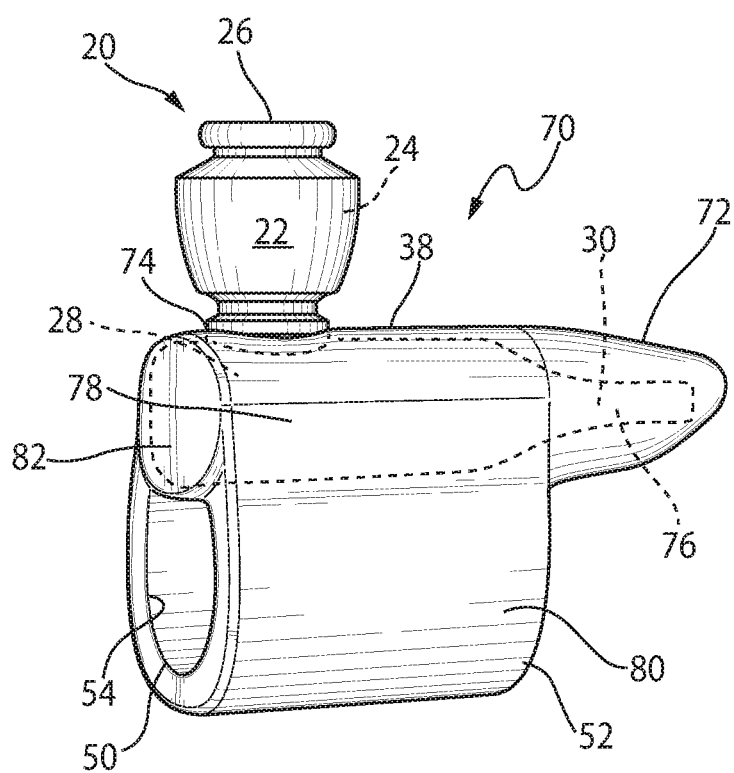
FIG. 5 is a side perspective view of an exemplary second embodiment of a sexual novelty device in accordance with the present disclosure.

Referring now to FIG. 5, another embodiment of the device 10 is generally designated 70. Components shared with the device 10 are designated with identical reference numbers. A major difference featured in the device 70 is that the pipe shank 28 is completely enclosed within an extended mouthpiece 72. The insertion opening 74 is accordingly located on the first surface 38 of the mouthpiece 72, and is dimensioned for accommodating insertion of the pipe 20 into the chamber 76 of the housing 78. In the device 70, the housing 78 is dimensioned for enclosing both the shank 28 and stem 30 portions of the pipe 20. In other words, in the device 70, the insertion opening 74 is positioned on a top portion of the "D"-shaped housing 78. Accordingly, a center axis of the insertion opening 74 is generally perpendicular to a longitudinal axis of the housing 78.

A feature of the device 70 is that since the shank 28 and stem 30 portions are enclosed in the housing 78, the user can optionally leave the pipe 20 in the chamber 76 during the replenishment of tobacco or other combustible material during use. For example, the bowl 22 can be rotationally removed from the pipe 20, leaving the rest of the pipe 20 in the housing 16 but partially exposing the shank 28 through the insertion opening 74. Thereafter, the bowl 22 with fresh tobacco can be attached back to the shank 28 through the insertion opening 74 without removing the pipe 20.

Another feature of the device 70 is that the penile band 80 is extended axially for enhanced penile gripping action. As seen in FIG. 5, the band 80 extends at least approximately ½ the axial length of the housing 78. While other configurations are contemplated, in the preferred device 70, the entry end 50 is preferably generally vertically aligned with the closed distal end 82. The opposite exit end 52 is located midway along the stem 30. Otherwise, the device 70 operates similarly to the device 10, including the provision of a bead region 60 and gripping formations 64.

While a particular embodiment of the present sexual novelty device with a smoking pipe has been described herein, it will be appreciated by those skilled in the art that changes and modifications may be made thereto without departing from the present disclosure in its broader aspects and as set forth in the following claims.

The invention claimed is:

1. A sexual novelty device, comprising:
a mouthpiece having a generally tubular housing that defines an inner chamber dimensioned for receiving a smoking pipe, said housing having an insertion opening configured for accommodating insertion of the smoking pipe, and an inhalation opening at a first end of said housing in fluid communication with said chamber configured for providing access to the smoking pipe by a user;
a penile band integrally formed with and vertically displaced from said housing, said penile band sharing a surface of said housing and constructed and arranged for resiliently engaging a penis;
said penile band has an entry end and an exit end, both said ends configured for accommodating the penis, said penile band fixedly attached to said housing, said entry end being generally aligned with said insertion opening; and
said entry end is generally aligned with a second end of said housing and extends at least approximately ½ a length of said mouthpiece.

2. The device of claim 1, wherein said device is made of an elastic material including at least one of silicone, natural rubber, synthetic rubber, copolymerized rubber, and elastomer, wherein said inner chamber of said housing is constructed and arranged for elastically and detachably gripping at least one of stem and shank portions of the pipe for rotatably securing the pipe in said chamber.

3. The device of claim 1, wherein said insertion opening is located at a second end of said housing and is dimensioned for accommodating insertion of the pipe into said chamber.

4. The device of claim 1, wherein said insertion opening is larger than said inhalation opening, said inhalation opening having a flexibly closable slit configured to facilitate user inhalation of smoke from a stem of the pipe.

5. The device of claim 1, wherein said penile band has a band length, said band length and said mouthpiece length extending in a common direction, said penile band being substantially closer to said insertion opening than said inhalation opening.

6. The device of claim 1, wherein said penile band has an exterior surface and an interior surface, said interior surface configured for engaging the penis, at least one of said exterior and interior surfaces having a beaded region, said beaded region having a plurality of spaced, hemispherical formations that project from said at least one surface.

7. The device of claim 6, wherein said interior surface is dimensioned for fitting around at least one of a shaft portion of the penis and behind testicles for repressing premature ejaculation and for prolonging an erection of the penis.

8. The device of claim 1, wherein said mouthpiece includes a first surface that is substantially dome-shaped in vertical cross-section and a second surface that is substantially flat, said second surface configured to directly abut a shaft of the penis.

9. The device of claim 8, wherein said second surface includes a plurality of spaced parallel ribs that extend transverse to a longitudinal axis of said mouthpiece for improving friction between said second surface and the shaft, preventing slippage of said mouthpiece from the penis.

10. The device of claim 8, wherein said insertion opening is located on said first surface and is dimensioned for accommodating insertion of the pipe into said chamber, and also facilitates attachment of a pipe bowl to a pipe shank.

11. A sexual novelty device, comprising:
a smoking pipe having segmented members, said segmented members including at least:
a pipe bowl having a cavity for receiving a combustible material and a holed cap for igniting the combustible material;
a pipe shank connected to the pipe bowl, the shank having an air way in fluid communication with the pipe bowl; and
a stem connected to the shank, the stem having a lip in fluid communication with the shank and the bowl for user inhalation;
and
a holder, including:
a mouthpiece having a generally tubular housing that defines an inner chamber dimensioned for receiving the smoking pipe, said housing having an insertion opening configured for accommodating insertion of the smoking pipe, and an inhalation opening at a first end of said housing in fluid communication with said chamber configured for providing access to the smoking pipe by a user; and
a penile band associated with said housing and constructed and arranged for resiliently engaging a penis.

12. The device of claim 11, wherein said housing thermally insulates at least one of the shank and the stem, and a length of said housing is greater than or equal to approximately a length of the stem.

13. The device of claim 11, wherein the smoking pipe is configured to be slidably insertable into said insertion opening such that the lip of the smoking pipe reaches said inhalation opening.

14. A sexual novelty device, comprising:
a mouthpiece having a generally tubular housing that defines an inner chamber dimensioned for receiving a smoking pipe, said housing having an insertion opening configured for accommodating insertion of the smoking pipe, and an inhalation opening at a first end of said housing in fluid communication with said chamber configured for providing access to the smoking pipe by a user;
a penile band integrally formed with and vertically displaced from said housing, said penile band sharing a surface of said housing and constructed and arranged for resiliently engaging a penis;
said mouthpiece includes a first surface that is substantially dome-shaped in vertical cross-section and a second surface that is substantially flat, said second surface configured to directly abut a shaft of the penis; and said insertion opening is located on said first surface and is dimensioned for accommodating insertion of the pipe into said chamber, and also facilitates attachment of a pipe bowl to a pipe shank.

\* \* \* \* \*